United States Patent [19]

Behler et al.

[11] Patent Number: 4,894,485

[45] Date of Patent: Jan. 16, 1990

[54] ALKALINE EARTH METAL SALTS OF ETHER CARBOXYLIC ACIDS AS ALKOXYLATION CATALYSTS

[75] Inventors: Ansgar Behler, Bottrop; Uwe Ploog, Haan; Elvira Scholz, Duesseldorf, all of Fed. Rep. of Germany

[73] Assignee: Henkel Kommanditgesellschaft auf Aktien, Duesseldorf, Fed. Rep. of Germany

[21] Appl. No.: 206,623

[22] Filed: Jun. 14, 1988

[30] Foreign Application Priority Data

Jun. 15, 1987 [DE] Fed. Rep. of Germany ....... 3719968
Jan. 25, 1988 [DE] Fed. Rep. of Germany ....... 3802044

[51] Int. Cl.$^4$ .............................................. C07C 41/03
[52] U.S. Cl. ..................................... 568/618; 568/678
[58] Field of Search ................ 568/618, 678, 680, 620

[56] References Cited

U.S. PATENT DOCUMENTS

| | | | |
|---|---|---|---|
| 3,775,052 | 11/1973 | Van Paassen | 8/137 |
| 3,917,676 | 11/1975 | Kisaki et al. | |
| 3,992,443 | 11/1976 | Springmann | 260/535 |
| 4,130,636 | 12/1978 | Tomlinson | 424/52 |
| 4,396,779 | 8/1983 | Edwards | 568/618 |
| 4,399,050 | 8/1983 | Bentham et al. | 252/95 |
| 4,453,022 | 6/1984 | McCain et al. | 568/618 |
| 4,478,281 | 10/1984 | Balzer et al. | 166/274 |
| 4,485,873 | 12/1984 | Balzer et al. | 166/274 |
| 4,549,275 | 10/1985 | Sukonick | 364/521 |
| 4,582,138 | 4/1986 | Balzer | 166/273 |

FOREIGN PATENT DOCUMENTS 0888761 12/1981 Belgium .
0082554 12/1982 European Pat. Off. .
0082569 6/1983 European Pat. Off. .
0085167 8/1983 European Pat. Off. .
0922256 10/1983 European Pat. Off. .
0115083 3/1986 European Pat. Off. .
2418444 12/1976 Fed. Rep. of Germany .
1526379 9/1978 United Kingdom .

OTHER PUBLICATIONS

Chemical Abstracts 98:217671c (equiv. to JP 82/202,391).
Chemical Abstracts 105:117028t (equiv. to JP 86/21,199).
Chemical Abstracts 103:217300c (equiv. to JP 85/158,298).
JOACS, vol. 63, No. 5 (May 1986).
HAPPI, May 1986.

Primary Examiner—Howard T. Mars
Attorney, Agent, or Firm—Ernest G. Szoke; Wayne C. Jaeschke; Real J. Grandmaison

[57] ABSTRACT

Alkaline earth metal salts of ether carboxylic acids corresponding to the following general formula $$[RO-(C_mH_{2m}O)_n-CH_2-COO^-]_x M^{2+} \qquad (I)$$

in which R represents $C_1-C_{22}$ alkyl, $C_3-C_{22}$ alkenyl, phenyl, alkylphenyl containing 1 to 3 $C_1-C_{15}$ alkyl radicals, benzyl or phenylethyl, M represents Ca, Sr or Ba, m is equal to 2 or 3, n is equal to 1 to 20 and x is equal to 2; or R is a group of the formula $-CH_2-COO^-$, x is equal to 1 and M, m and n are as defined above, are used as catalysts for the ethoxylation or propoxylation of organic compounds containing active H atoms. They afford advantages by virtue of the solubility of the catalysts in the reaction medium and provide for a narrow homolog distribution of the polyalkoxylation products.

8 Claims, No Drawings

ALKALINE EARTH METAL SALTS OF ETHER CARBOXYLIC ACIDS AS ALKOXYLATION CATALYSTS

BACKGROUND OF THE INVENTION

1. Field of the Invention

This invention relates to the use of alkaline earth metal salts of ether carboxylic acids as catalysts for the ethoxylation or propoxylation of organic compounds containing active H atoms.

2. Discussion of Related Art

Organic compounds containing active H atoms are understood to be, for example, fatty alcohols, fatty acids and amines, which are formed in the ethoxylation or propoxylation of nonionic detergents. One typical example is the reaction of a fatty alcohol generally containing 10 to 18 carbon atoms with ethylene oxide or propylene oxide in the presence of a catalyst, the fatty alcohol reacting with several molecules of ethylene oxide or propylene oxide.

Catalysts which have been used for the polyalkoxylation reaction mentioned above include, inter alia, the following compounds: calcium and strontium hydroxide, alkoxides and phenoxides as disclosed in EP-A 0 092 256; calcium alkoxides as disclosed in U.S. Pat. No. 4,396,779; barium hydroxide as disclosed in EP 0 115 083; basic magnesium compounds, for example alkoxides as disclosed in EP 0 082 569; and magnesium and calcium fatty acid salts as disclosed in EP 085 167.

The catalysts mentioned above are attended, inter alia, by the disadvantage that they are difficult to incorporate in the reaction system or are difficult to produce.

Other conventional polyalkoxylation catalysts include potassium hydroxide and sodium methylate.

A narrow range of the degree of polyalkoxylation is of particular importance for fatty alcohol polyalkoxylates, cf. JAOCS, Vol. 63 691–695 (1986) and HAPPI, 5 (1968) pp. 52, 54, 123. Accordingly, so-called "narrow-range" alkoxylates primarily have the following advantages: low pour points; relatively high smoke points; fewer mols alkoxide to acquire solubility in water; less hydrotrope for introduction into liquid detergents; a relatively faint odor due to the presence of free (unreacted) fatty alcohols; and reduction of pluming in the spray-drying of detergent slurries containing fatty alcohol polyalkoxylate surfactants.

The range or homolog distribution of fatty alcohol polyalkoxylates is critically determined by the type of catalyst used. A measure of the homolog distribution is the so-called Q value according to the following equation:

$$Q = \bar{n} \cdot p^2$$

where $\bar{n}$ is the mean adduct number (mean degree of ethoxylation) and p is the percentage of adduct having a certain ethylene oxide (EO) degree which is predominantly formed. Accordingly, a high Q value signifies a narrow homolog distribution range.

The ether carboxylic acids on which the alkaline earth metal salts to be used in accordance with the invention are based are known compounds which are commercially available and which may be prepared, for example, in accordance with German Pat. No. 24 18 444. The alkali metal and alkaline earth salts of these ether carboxylic acids are also known per se and have been used as highfoam surfactants with skin-care properties, for example in personal hygiene preparations (Japan 86/21 199), in cosmetic and pharmaceutical formulations (German 3 521 505, Japan 82/202 391), in cleaning formulations (Japan 85/158 298, Belgium 888 761) and as tasteless surfactants in toothpastes (U.S. Pat. No. 4,130,636, GB 1,526,379) and also in upholstery shampoos (U.S. Pat. No. 3,775,952) and as surfactants in tertiary oil recovery (U.S. Pat. No. 4,582,138, U.S. Pat. No. 4,485,873 and U.S. Pat. No. 4,478,281).

DESCRIPTION OF THE INVENTION

Other than in the operating examples, or where otherwise indicated, all numbers expressing quantities of ingredients or reaction conditions used herein are to be understood as modified in all instances by the term "about".

It has now been found that polyethoxylated or polyproxylated fatty alcohols having a high Q value can be obtained using the alkaline earth salts of ether carboxylic acids corresponding to formula I below in accordance with the invention. More specifically, alkaline earth metal salts of ether carboxylic acids corresponding to the following general formula $$[RO-(C_mH_{2m}O)_n-CH_2-COO^-]_x M^{2+} \quad (I)$$

in which

R is a substituent selected from the group consisting of $C_1$–$C_{22}$ alkyl, $C_3$–$C_{22}$ alkenyl, phenyl, alkylphenyl containing 1 to 3 $C_1$–$C_{15}$ alkyl radicals, benzyl and phenylethyl, M is an alkaline earth metal selected from the group consisting of Ca, Sr and Ba, m is the number 2 or 3, n is a number from 1 to 20 and x is the number 2; or R is a group corresponding to the following formula $$-CH_2-COO^-$$

x is the number 1, and

M, m and n are as defined above, are used as catalysts for the ethoxylation or propoxylation of organic compounds containing active H atoms. The alkaline earth metal salts to be used in accordance with the invention have the advatage over known catalysts in that they provide for short reaction times and, by virtue of their alcohol solubility, are soluble in the reaction system in contrast, for example to state-of-the-art alkaline earth metal salts.

The ether carboxylic acids of general formula I on which the alkaline earth metal salts to be used in accordance with the invention are based are generally derived from a polyalkoxylated α-hydroxyacetic acid, the polyalkoxyl groups being formed by ethylene oxide or propylene oxide or by ethylene oxide and propylene oxide in random or block distribution. Where they are formed with propylene oxide, the exact position of the methyl groups cannot be stated. Ether carboxylic acids of which the polyalkoxy chain is formed solely by ethylene oxide (m=2) are preferred. The free hydroxyl group of the polyalkoxy chain is etherified with an alcohol or phenol of the formula ROH, where R is selected from the group consisting of linear or branched $C_1$–$C_{22}$ alkyl, linear or branched $C_3$–$C_{22}$ alkenyl, phenyl, alkylphenyl containing 1 to 3 $C_1$–$C_{15}$ alkyl radicals, benzyl and phenylethyl. Alkaline earth metal salts of ether carboxylic acids, in which the group R is a $C_1$–$C_8$ alklyl group, are preferred because these compounds are soluble in methanol. The more highly alkylated derivatives are only soluble in alcohols higher than methanol, although they may also readily be used as alkoxylation catalysts in accordance with the invention.

It is also preferred to use alkaline earth metal salts of ether carboxylic acids corresponding to general formula I in which n is a number of 1 to 12. Compounds in which n has a value of greater than 20 are less preferred because they do not show optimal catalytic activity.

The calcium, strontium and barium soaps to be used in accordance with the invention may be obtained by known processes for the production of alkaline earth soaps of carboxylic acids.

According to the invention, the alkaline earth salts of ether carboxylic acids corresponding to general formula I are used as catalysts in a quantity of 0.1 to 2% by weight, based on the end product of the ethoxylation or propoxylation reaction.

The invention is illustrated in the following with respect to preferred embodiments herein.

The following describes the general procedure for the preparation of calcium, strontium or barium salts of alkaline earth metal salts of ether carboxylic acids corresponding to general formula I. The ether carboxylic acids are dissolved or suspended in a mixture of water, ethanol and isopropanol (3:2:1) and reacted at 90° C. with equimolar quantities of calcium, strontium or barium acetate, the quantity being calculated from the acid value. The acetic acid released was distilled off with the solvent.

The catalysts summarized in Table I below were used.

TABLE I

| Catalysts produced corresponding to general formula I | | | | | |
|---|---|---|---|---|---|
| Catalyst no. | R | m | n | x | M |
| 1 | $C_{12-14}$ | 2 | 3.8 | 2 | Ba |
| 2 | $C_{12-18}$ | 2 | 9 | 2 | Ba |
| 3 | $CH_2COO$ | 2 | 3 | 1 | Ca |
| 4 | $C_{12}$ | 2 | 4 | 2 | Ca |
| 5 | $C_8$ | 2 | 3 | 2 | Ca |
| 6 | $C_8$ | 2 | 5 | 2 | Ca |
| 7 | $C_8$ | 2 | 5 | 2 | Ba |
| 8 | $C_8$ | 2 | 5 | 2 | Sr |

TABLE II

Ethoxylation of a commercial lauryl alcohol (Lorol ® $C_{12}$) using catalysts of formula I

| Cat. no. | Cat. % | t (h) | Q | FFA (%) | OH value actual | OH value desired |
|---|---|---|---|---|---|---|
| 1 | 0.5 | 6.5 | 1,279 | 4.6 | 131.2 | 125.2 |
| 2 | 0.5 | 7.5 | 850 | 4.4 | 128.1 | 122.2 |
| 3 | 0.5 | 6.0 | 1,100 | 4.9 | 136 | 126.3 |
| 4 | 0.5 | 7.0 | | | 116.6 | 125.2 |
| 5 | 0.5 | 11.0 | 1,112 | 5.0 | 134.1 | 123.7 |
| 6 | 0.5 | 6.5 | 1,086 | 5.9 | 137.7 | 128.9 |
| 7 | 0.5 | 3 | 1,006 | 5.3 | 131.8 | 130.0 |
| 8 | 0.5 | 3 | 983 | 4.4 | 135.8 | 127.0 |

The following describes the ethoxylation with the catalysts of general formula I to be used in accordance with the invention. The catalyst was dissolved in the substance to be ethoxylated. The solution was transferred to an autoclave suitable for the alkoxylation. The autoclave was purged with nitrogen and evacuated for 30 minutes at a temperature of 100° C. The temperature was then increased to 180° C. The desired quantity of ethylene oxide was introduced under a pressure of 5 bar. On completion of the reaction, the reaction mixture was left to after-react for 30 minutes.

The results obtained with the catalysts used in accordance with the invention in the ethoxylation of a commercial lauryl alcohol (Lorol ® $C_{12}$) as described above are shown in Table II where;
Q=the Q value defined above,
OH value, actual/desired=OH values of the polyethoxylated lauryl alcohols obtained as end product,
Cat-%=catalyst concentration, based on the end product,
FFA=content of free fatty alcohols in the end product in area-% (GC analysis), and
t=polyethoxylation reaction time.

The results of comparison tests using known catalysts are shown in Table III. A commercial lauryl alcohol is again polyethoxylated. The comparison shows that the compounds according to the invention give better homolog distributions (higher Q values) than potassium hydroxide, sodium methylate and calcium hydroxide. They also give equally good results compared to barium hydroxide, calcium oleate and calcium stearate, but in contrast to these compounds are soluble in the reaction mixture. Calcium ethylate, which also gives equally good results, is much more difficult to produce and can only be handled with difficulty.

TABLE III

Ethoxylation of a commercial lauryl alcohol (Lorol ® $C_{12}$) using known catalysts

| Catalyst | Cat.-% | Reaction time (h) | Q | OH value actual | OH value desired | FFA (%) |
|---|---|---|---|---|---|---|
| KOH | 0.5 | 3.5 | 611 | 125.1 | 125.2 | 7.5 |
| $NaOCH_3$ | 0.5 | 4.0 | 595 | 128.8 | 126.8 | 9.9 |
| $Ca(OH)_2$ | 0.5 | 11.0 | 695 | 136.8 | 126.3 | 9.4 |
| $Ba(OH)_2$ | 1.0 | 4.0 | 1225 | 129.3 | 128.4 | 3.8 |
| Ca oleate | 0.5 | 10.5 | 1272 | 126.7 | 128.4 | 5.1 |
| Ca stearate | 1.0 | 7.5 | 1251 | 132.8 | 129.5 | 5.0 |
| Ca ethylate | 0.5 | 8.0 | 1316 | 130.2 | 125.7 | 4.5 |

We claim:

1. The process of ethoxylating or propoxylating a fatty alcohol consisting essentially of contacting said fatty alcohol with ethylene oxide or propylene oxide in the presence of from about 0.1 to about 2% by weight, based on the weight of the ethoxylated or propoxylated compound, of an alkaline earth metal salt of an ether carboxylic acid corresponding to the following formula $$[RO-(C_mH_{2m}O)_n-CH_2-COO^-]_xM^{2+} \qquad (I)$$

in which
R is a substituent selected from the group consisting of $C_1$-$C_{22}$ alkyl, $C_3$-$C_{22}$ alkenyl, phenyl, alkylphenyl containing 1 to 3 $C_1$-$C_{15}$ alkyl radicals, benzyl and phenylethyl,
M is an alkaline earth metal selected from the group consisting of Ca, Sr and Ba,
m is the number 2 or 3,
n is a number from 1 to 20 and
x is the number 2; or
R is a group corresponding to the following formula $$-CH_2-COO^-$$

x is the number 1 and
M, m and n are as defined above.

2. The process as in claim 1 wherein m is the number 2.

3. The process as in claim 1 wherein R is a $C_1$-$C_8$ alkyl radical.

4. The process as in claim 1 wherein n is a number from 1 to 12.

5. The process of ethoxylating or propoxylating a fatty alcohol consisting essentially of contacting said fatty alcohol with ethylene oxide or propylene oxide in the presence of from about 0.1 to about 2% by weight, based on the weight of the ethoxylated or propoxylated compound, of a catalyst consisting essentially of an alkaline earth metal salt of an ether carboxylic acid corresponding to the following formula $$[RO-(C_mH_{2m}O)_n-CH_2-COO^-]_xM^{2+} \quad (I)$$

in which

R is a substituent selected from the group consisting of $C_1$-$C_{22}$ alkyl, $C_3$-$C_{22}$ alkenyl, phenyl, alkylphenyl containing 1 to 3 $C_1$-$C_{15}$ alkyl radicals, benzyl and phenylethyl, M is an alkaline earth metal selected from the group consisting of Ca, Sr and Ba, m is the number 2 or 3, n is a number from 1 to 20 and x is the number 2; or R is a group corresponding to the following formula $$-CH_2-COO^-$$

x is the number 1 and

M, m and n are as defined above.

6. The process as in claim 5 wherein m is the number 2.

7. The process as in claim 5 wherein R is a $C_1$-$C_8$ alkyl radical.

8. The process as in claim 5 wherein n is a number from 1 to 12.

* * * * *